United States Patent [19]

Terrell et al.

[11] 4,365,097

[45] Dec. 21, 1982

[54] PROCESS FOR THE PREPARATION OF HALOGENATED ALIPHATIC ETHERS

[75] Inventors: Ross C. Terrell, Clark; Kirsten Hansen, Berkeley Heights, both of N.J.

[73] Assignee: Airco, Inc., Montvale, N.J.

[21] Appl. No.: 244,384

[22] Filed: Mar. 16, 1981

Related U.S. Application Data

[63] Continuation-in-part of Ser. No. 63,302, Aug. 2, 1979, abandoned.

[30] Foreign Application Priority Data

| | | |
|---|---|---|
| May 20, 1980 [CA] | Canada | 352253 |
| Jun. 5, 1980 [IT] | Italy | 22578 A/80 |
| Jul. 21, 1980 [FR] | France | 80 16062 |
| Jul. 24, 1980 [GB] | United Kingdom | 8024272 |
| Jul. 31, 1980 [DE] | Fed. Rep. of Germany | 3029134 |

[51] Int. Cl.$^3$ ............................................. C07C 41/01
[52] U.S. Cl. ..................................... 568/684; 568/683
[58] Field of Search ............................... 568/684, 683

[56] References Cited

U.S. PATENT DOCUMENTS 2,332,467  10/1943  Linn et al. ........................... 568/671
3,931,238   1/1976  Starks ................................. 568/671

OTHER PUBLICATIONS

Freedman et al., Tetrahedron Letters, No. 38, pp. 3251–3254, 1975.
Herreott et al., Tetrahedron Letters, No. 44, pp. 4521–4524, 1972.
Corley et al., J. Am. Chem. Soc., 78, pp. 3489–3492, 1956.
Scipioni et al., Translation Ann. Chim. Rome, 1967, 57(7), 817–824.

*Primary Examiner*—Howard T. Mars
*Attorney, Agent, or Firm*—Roger M. Rathbun; Larry R. Cassett

[57] ABSTRACT

Processes for the preparation of certain halogenated aliphatic ethers are described, and in particular the preparation of 1,1,2-trifluoro-2-chloroethyl methyl ether, i.e., $CH_3OCF_2CHFCl$. This particular ether has many uses, and is a valuable material for use in the production of the inhalant anesthetic enflurane, 1,1,2-trifluoro-2-chloroethyl difluoromethyl ether, i.e., $CF_2HOCF_2CHFCl$, made and sold under the trademark ETHRANE by Airco, Inc., Montvale, New Jersey 07645.

11 Claims, No Drawings

PROCESS FOR THE PREPARATION OF HALOGENATED ALIPHATIC ETHERS

This is a continuation-in-part of application Ser. No. 63,302, filed Aug. 2, 1979, now abandoned.

FIELD OF THE INVENTION

The present invention relates to processes for the preparation of certain halogenated aliphatic ethers. More particularly, the present invention relates to the preparation of such halogenated ethers from certain perhalogenated alkanes.

BACKGROUND OF THE INVENTION

One commercial process for the manufacture of 1,1,2-trifluoro-2-chloroethyl methyl ether is a two-step process, as follows:

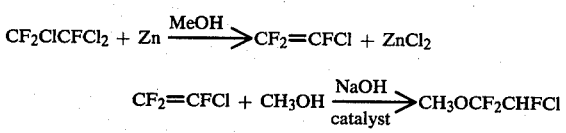

The first step in this process is expensive because it involves the preparation of the gas $CF_2=CFCl$, which must be distilled under pressure or at low temperature. The solvent methanol must be recovered from the by-product zinc chloride, and disposal of the zinc chloride is a problem.

The second step of this synthesis is efficient, but requires a separate reactor and purification system.

The reaction of certain perhalogenated alkanes with a primary or secondary alkanol and an inorganic base to produce certain halogenated ethers is described in Corley et al, JACS 78, on p. 3491, bottom of col. 1, as follows:

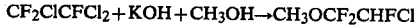

The text of this article indicates a reaction at 125° for 20 hours, and then:

"The product was taken up in diethyl ether, washed with water, dried and fractionated through a 30-plate column to give a 30% yield (range 20–36%) of $CH_3OCF_2CHFCl$ ... "

The results obtained by Corley, in a reaction without a catalyst, generally showed low yields and conversions, and relatively long reaction times.

An article by Scipioni et al, Ann. Chem. Rome, 1967, 57(7), pgs. 817–824, also discusses the reactivity of various halogenated alkanes with alkanols and inorganic bases to product ethers therefrom.

In *Fluorine Chemistry Reviews*, by Metille and Burton, p. 354, the authors describe the dehalogenation of $CF_3I$ to $CF_3H$, using KOH in a solvent of high dielectric constant, specifically referred to ethanol. The use of the reaction to dehalogenate $CF_3CF_2I$ to $CF_3CF_2H$ is also discussed.

The source article referred to by Metille and Burton is Banus et al., J. Chem. Soc. 1951, pp. 60–64. This publication states that it is known that the C-I bond in $CF_3I$ can undergo homolytic fission but that, apart from decomposition, $CF_3Cl$, $CF_2Cl_2$ and $CHF_2Cl$ "do not show reactions involving the homolytic or heterolytic fission of the carbon-chloride bond". The publication in general stresses that the iodo compounds are unique as compared to the corresponding bromo or chloro compounds. It would not, therefore, suggest the use of the same type of reaction even for brominated, chlorinated, or fluorinated alkanes, let alone ethers.

Dittman, 2,636,908 relates to dehydrochlorination in the presence of caustic or KOH, to produce $CF_2=CClF$. Alcohol was not used. Other references to dehydrohalogenation may be found in Frederick, U.S. Pat. No. 2,709,181; Young, U.S. Pat. No. 3,391,204, Ex. 15; Miller, U.S. Pat. Nos. 2,803,665 and 2,803,666; Tarrant et al, JACS 76, 2343 at 2344 (1954) and Corley et al, supra at 3489 (1956).

One addition of an alcohol to an olefinically unsaturated perhaloethylene is described in Corley et al, supra, 78 JACS at 3491, where the following reaction is described:

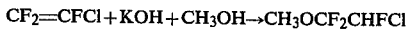

Park et al, in JACS 70, 1550 (1948), describe the addition of methanol and ethanol to $CF_2=CFCl$. Hanford, U.S. Pat. No. 2,409,274 describes an addition reaction of an unsaturated substrate with an alcohol in the presence of a base, to produce an ether, as follows:

Another description of a similar alcohol addition reaction appears in Aliphatic Fluorine Compounds, Lovelace et al., Reinhold, 1958, pp. 155–159.

The Lovelace et al text, supra, describes the reaction between fluorocarbon halides and alcoholates as generally producing ethers, citing several examples. The Tarrant and Young work, JACS 75, 932 (1953), is relied upon by Lovelace et al as establishing that the general reaction is not a simple Williamson synthesis.

Young, U.S. Pat. No. 3,391,204 describes the reaction between a perhalogenated fluoro-chloro-substituted alkane and TEA (Ex. 11), which may be in the presence of $CuCl_2$ (Ex. 12; Col. 7, 11, 6-25) and methanol (Col. 6, 1. 74) or other alkanol (Col. 6, 11, 68–69). The alcohol or other solvent is considered to be an inert diluent (Col. 6, 11, 28, et seq.). Generally, the reaction extracts a chlorine and replaces it with a hydrogen, as in Exs. 7, 8, 11 and 12, but the reaction may go one step further with a dehydrohalogenation step occurring (Exs. 7, 8 and 15) with the production of an ethylenically unsaturated product. Young's reactions do not produce ethers.

Park et al report in JACS 70, at 1550, that:

"Alkyl ethers containing fluorine were previously prepared by Swartz by the action of alcoholic caustic or metallic carbonate on polyfluorohaloethanes. This procedure was later modified by Gowland."

The Gowland reference is to British Pat. No. 523,449, which describes the following reaction:

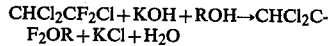

Gowland's initial reaction is not perhalogenated.

Other reactions are known in which a halogenated alkane is reacted with an alcohol and an inorganic base, to produce a halogenated ether, but the halogenated alkane is not a perhalogenated compound, as in the present invention, and the reaction mechanism is that of dehydrohalogenation, rather than reduction. These include U.S. Pat. No. 3,637,477, granted Jan. 25, 1972, to L. S. Croix, and assigned to Air Reduction Co., Inc.; and J. Gen. Chem. (U.S.S.R.), 29, 1113-1117 (1959), Soborovskii and Baina, Difluorochloromethane as a Difluoromethylating Agent.

The presence of hydrogen substituents in the halogenated alkane, and its chain length, also affect the reaction. Thus, Tarrant et al, JACS 76, at p. 2344, state:

" . . . CH$_2$ClCH(CH$_3$)CH=CF$_2$ . . . is the product which would be expected from CH$_2$ClCH(CH$_3$)CH$_2$CF$_2$Cl, since it has been shown that the point of attack by a base on molecule containing fluorine is the hydrogen on a carbon adjacent to a cluster of fluorine atoms on a single atom."

with a citation to Tarrant and Young, JACS 75, 932 (1953).

U.S. Pat. No. 3,931,238 to Starks discloses the preparation of various alcohols and ethers from halogenated hydrocarbons. In particular, this patentee employs various betaines as catalysts in connection with aqueous alkali metal hydroxide solutions. This patentee does not employ any primary or secondary alkanol reactants, however, and among the betaines includes certain quaternary ammonium salts. No primary, secondary or tertiary amines are said to be useful as catalysts therein. As a matter of fact, this patentee specifically shows in Example 1 that one tertiary amine is comparatively highly inferior to his betaines and excluded from his invention.

Finally, U.S. Pat. No. 2,332,467 to Linn et al relates to the production of mixed ethers by contacting an alcohol with an alkyl halide and zinc at elevated temperatures.

SUMMARY OF THE INVENTION

In accordance with the present invention it has now been discovered that in the reaction of certain perhalogenated alkanes (preferably ethanes) such as CF$_2$ClCFCl$_2$ (Freon 113) with a primary or secondary alkanol (ROH) and an inorganic base, for the production of particular ethers, the reaction can be greatly improved, for example over that disclosed in the aforementioned Corley article, by the use of a particular type of catalyst, in terms of improved reaction times, better yields, higher conversions, lower operating temperatures, etc. Also, the reaction may be advantageously carried out with these results being obtained at atmospheric pressure.

The particular type of catalyst system in question includes (1) certain specific varivalent metal-containing catalysts. In particular, such catalysts thus include either copper in its metallic (elementary) form, preferably in a finely divided metallic state, or the following metals in the form of their corresponding metal salts; copper, silver, cobalt, rubidium, aluminum, manganese, nickel, iron, molybdenum, chromium, antimony, and vanadium, and/or (2) the primary, secondary and tertiary amines.

The present invention is limited to certain specific perhalogenated alkanes which are useful in this reaction.

First, these compounds must have at least one carbon with the configuration CXF$_2$, where X=Cl or Br. Thus, the perhalogenated ethane may be represented as:

CXF$_2$CY$_3$

Since CXF$_2$ is not reduced, CY$_3$ must be a reducible group where at least two of the Y's must be Br or Cl.

Thus, the general formula for suitable perhalogenated ethanes for use in the reaction of the invention is:

CXF$_2$CY$_2$Z where
X=Br or Cl
Y=Br or Cl
Z=Br, Cl or F.

Using this description, there are 14 suitable perhalogenated ethanes, which can be reacted according to the invention to produce ethers, as follows:

| Starting Perhalogenated Ethane | Ether Product |
|---|---|
| 1. CF$_2$ClCCl$_2$F | RO—CF$_2$CHFCl |
| 2. CF$_2$ClCBr$_2$F | RO—CF$_2$CHFBr |
| 3. CF$_2$ClCBrClF | RO—CF$_2$CHFCl |
| 4. CF$_2$ClCCl$_3$ | RO—CF$_2$CCl$_2$H |
| 5. CF$_2$ClCCl$_2$Br | RO—CF$_2$CCl$_2$H |
| 6. CF$_2$ClCBr$_3$ | RO—CF$_2$CHBr$_2$ |
| 7. CF$_2$ClCBr$_2$Cl | RO—CF$_2$CHClBr |
| 8. CF$_2$BrCCl$_2$F | RO—CF$_2$CHFCl |
| 9. CF$_2$BrCBr$_2$F | RO—CF$_2$CHFBr |
| 10. CF$_2$BrCBrClF | RO—CF$_2$CHFBr |
| 11. CF$_2$BrCCl$_3$ | RO—CF$_2$CHCl$_2$ |
| 12. CF$_2$CrCCl$_2$Br | RO—CF$_2$CHCl$_2$ |
| 13. CF$_2$BrCBr$_3$ | RO—CF$_2$CHBr$_2$ |
| 14. CF$_2$BrCBr$_2$Cl | RO—CF$_2$CHClBr |

DETAILED DESCRIPTION

A particularly useful application of the invention is in the conversion of CF$_2$ClCFCl$_2$ to CH$_3$OCF$_2$CHFCl by reaction with methanol and a base such as sodium hydroxide, sodium methylate, and the like, in the presence of a catalyst, as is described in greater detail in some of the examples below.

In this particular case, the ether product and methanol form a unique azeotrope that facilitates separation and recovery.

The use of the specific catalysts set forth above have been found essential in obtaining the improved yields, conversions, and reduced reaction times (such as over the reaction described in the Corley reference).

As indicated above, the primary, secondary, and tertiary amines, including cyclic amines, and diamines may be used as the catalysts hereof, either alone or preferably in combination with the aforesaid metal-containing catalysts. Preferably, the primary, secondary and tertiary alkanol amines are so utilized. Other suitable amines which may be employed as the catalysts hereof include:

| | |
|---|---|
| Methylamine (monomethylamine) | Aniline |
| Dimethylamine | Pyridine |
| Diethylamine | Ethylene diamine |
| Triethylamine | N,N,N—trimethyl ethylene diamine |
| Isopropyl-amine | |
| Di-n-propylamine | Diazo bicyclo (2,2,2) octane |
| Piperidine | |
| Morpholine | N,N—diethyl ethylene diamine |
| Monoethanolamine | |
| Diethanolamine | 1,2-cyclohexylene dinitrilo acetic acid |
| Hydrazine | |
| Ethylenediamine tetraacetic acid | 3-dimethylamino propylamine |
| Triethylene tetramine | N—(2-amino ethyl morpholine) |

The metal-containing catalysts hereof may be in a finely divided or other suitable state. The catalyst may be copper in its metallic (elementary) state or in the form of the metal salt of an inorganic or organic acid, such as the chloride, bromide, nitrate, acetate, propionate, etc. of copper, silver, cobalt, rubidium, aluminum, manganese, nickel, iron, molybdenum, chromium, antimony and vanadium. Preferably, the metal will comprise copper, i.e., as metallic copper or in the form of a copper salt of an inorganic or organic acid. Preferably a copper-containing catalyst, such as elementary copper in powder form or a cuprous or cupric salt, is employed.

As is further noted above, combinations of the amine and metal-containing catalysts may be utilized in the present process. A highly preferred catalyst is a mixture of cuprous chloride and triethanolamine.

The alkanol reactant is a primary or secondary alcohol, preferably a 1 to 4 carbon alkanol (i.e., a lower primary or secondary alkanol), but such alkanols of any known chain length up to about 12 carbons are usable and can be expected to be effective, although even higher alcohols are operative. Since the alcohol is a reactant and is incorporated into the final product, the choice of alcohol depends only on the product desired, i.e., $CH_3OH$ gives $CH_3OCF_2CY_2H$, $CH_3CH_2OH$ gives $CH_3CH_2OCF_2CY_2H$, etc.

The inorganic base may be an alkali metal dissolved in the alkanol, an alkali metal or alkaline earth metal hydroxide, dry or in aqueous solution; or any strongly basic material that does not interfere with the desired reaction, such as, for example, ammonia or sodium carbonate.

In operating the process of this invention, the alkanol may be employed in excess over the theoretical amount required to effect the desired conversion to an ether, and functions both as a reactant and as a solvent, and may be present in substantial excess for that reason. The base may also be used in excess. The limits on the proportions of each reactant employed are those established by the practical considerations of reaction kinetics, and ease of recovery of the product.

The temperature of the reaction is dependent upon the particular reactants employed and the desired product, and may be in the range, for example, from about 0° C. to about 100°–120° C. or higher and, preferably, from about 20° C. to about 80° C. The temperature and/or pressure are such that the reaction mass is in the liquid state during the course of the reaction. The reaction is exothermic and once initiated, may require cooling, depending upon equipment available and other conditions.

In general, the time of the reaction depends upon the particular reactants employed, the temperature of the reaction, the efficacy of the catalyst, and other influencing factors. Generally a few hours is adequate to produce a suitable yield of any desired product.

One advantage of the present reaction utilizing a catalyst is that it may be carried out at atmospheric pressure. The pressure of reaction seems to have no material effect on the course of the reaction.

The product may be isolated by any suitable means from the reaction mass. Ordinarily, the product is isolated by distillation from the reaction mass at atmospheric or subatmospheric pressure, depending upon the boiling point of the reaction product, with the reaction products being recovered as the distillate. Another acceptable technique for recovery of the ether product of Eq. 3 (infra) is to water-wash the crude product to remove amines, and any water-soluble reaction products and by-products, and to cause precipitation of insolubles.

A general equation for a preferred reaction in accordance with this invention is:

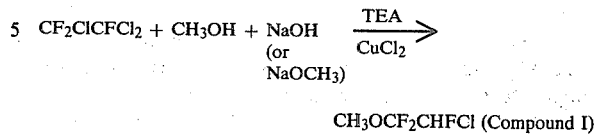

$$CH_3OCF_2CHFCl \text{ (Compound I)}$$

There appear to be three steps in this conversion reaction, which can be represented by equations, as follows:

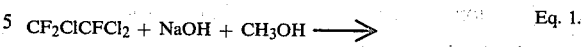

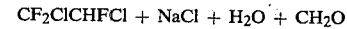

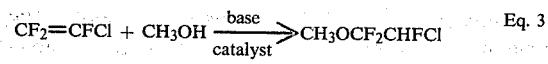

In order for the addition reaction to occur in Eq. 3, it is apparent that the unsaturated compound in Eq. 2 should have the configuration $$CF_2=CX_2$$

where X is Cl or Br.

The ether products of Eq. 3 are generally known chemicals, and also have a variety of uses. Thus, the production of Compound I by the reaction where the initial halogenated alkane reactant is $CF_2ClCFCl_2$, the alkanol is methanol, and the recovered product is $CH_3OCF_2CHFCl$ (Compound I), is of importance with respect to the production of the respiratory anesthetic enflurane, $CHF_2OCF_2CHFCl$, for which Compound I is a valuable intermediate.

In the production of Compound I, the reaction described in the general equation above is particularly useful because methanol forms a low boiling azeotrope with Compound I, which facilitates separation by distillation. Methanol can then be easily separated from the distillate by washing with water.

Thus, during the course of reacting $CH_3OH$, $NaOH$ and $CF_2ClCFCl_2$ in the presence of specific catalysts, to prepare $CH_3OCF_2CHFCl$, this compound and methanol form an azeotropic mixture, b.p. 56° containing 86% $CH_3OCF_2CHFCl$ and 14% $CH_3OH$. This azeotrope allows a convenient separation of the product from the excess methanol. If no azeotrope were formed it would be difficult to separate $CH_3OCF_2CHFCl$, b.p. 70°, and excess methanol, b.p. 64°, by distillation, since all the methanol would have to be removed as overhead.

The process of the invention also has other useful applications, and other alcohols and haloethanes may also be reacted to produce halogenated ethers. For example:

$$CF_2ClCFCl_2 + NaOH + CH_3CH_2OH \rightarrow CH_3CH_2OCF_2CHFCl + NaCl + H_2O + CH_3CHO$$

and $$CF_2ClCCl_3 + NaOH + CH_3OH \rightarrow CH_3OCF_2CHCl_2 + NaCl + H_2O + CH_2O$$

$CH_3OCF_2CHCl_2$ is the formula for the valuable anesthetic, methoxyflurane, and the preceding equation represents a valuable new synthetic route for its preparation.

To explain the invention further, several demonstrations of it are reported in the following examples. All temperatures are in °C., and all parts and percentages by weight, unless expressly stated to be otherwise. The equations in this application are intended to illustrate the nature of the several reactions, and are not necessarily balanced.

EXAMPLE 1

Dechlorination, Methanol Addition Reaction $CF_2ClCFCl_2 + NaOH + CH_3OH \rightarrow CH_3OCF_2CHFCl$ (Product 1)

EXAMPLE 1A

Reaction Without Catalysis

A mixture of $CF_2ClCFCl_2$ (94 g., 0.5 mole) 50% aqueous sodium hydroxide solution (120 g., 1.5 moles) and methanol (500 ml) was refluxed for twenty-four hours. The reaction mixture was distilled to give 91 g. of product b.p. 36°–62° C. This product was analyzed by gas chromatography in order to determine the percentages of $CH_3OCF_2CHFCl$, recovered by $CF_2ClCFCl_2$, and methanol present. The conversion to $CH_3OCF_2CHFCl$ (Product 1) was 19% and 75% of the $CF_2ClCFCl_2$ was recovered unchanged. The yield of $CH_3OCF_2CHFCl$ (Product 1) was about 76%, i.e., 19/25 (100%).

Product 1 is a valuable material for use in the production of the gaseous anesthetic enflurane, of the formula $CHF_2OCF_2CHFCl$. It is produced from Product 1 by the following route:

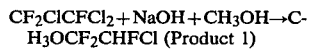
$CH_3OCF_2CHFCl \xrightarrow{\text{chlorination}} CHCl_2OCF_2CHFCl$ $\xrightarrow{\text{fluorination}} CHF_2OCF_2CHFCl$ (enflurane)

EXAMPLE 1B

Reaction with Catalysis

The foregoing reaction was essentially repeated, but with catalysis, in accordance with the equation:

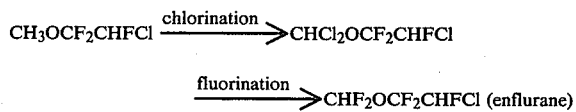
$CF_2ClCFCl_2 + CH_3OH + NaOH \xrightarrow[\text{TEA}]{\text{CuCl}_2}$ $CH_3OCF_2CHFCl$ (Product 1)

A mixture of $CF_2ClCFCl_2$ (94 g., 0.5 mole), 50% aqueous sodium hydroxide solution (120 g., 1.5 moles), methanol (500 ml), $CuCl_2$ (5 g.), and triethanolamine (5 g.) was refluxed for 24 hours. The reaction mixture was distilled to give 59.5 g. of product containing 94% $CH_3OCF_2CHFCl$. No starting material was recovered; thus the conversion to $CH_3OCF_2CHFCl$ was about 76% and the yield was about 76%.

A repetition of the reaction using 5 g. of $CrCl_3$ (chromium chloride) in place of copper chloride produced 45.7 g. of water-washed product (primarily $CH_3OCF_2CHFCl$, b.p. 50°–62° C.) and 1.7 g. believed to be unreacted or partially reacted material (b.p. 42°–49°). The conversion to $CH_3OCF_2CHFCl$ (Product 1) was 57% and the yield was about 57%.

EXAMPLE 2

Other Alkali and Alcohol Reactants for the Dechlorination, Methanol Addition Reaction

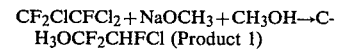
$CF_2ClCFCl_2 + NaOCH_3 + CH_3OH \rightarrow CH_3OCF_2CHFCl$ (Product 1)

EXAMPLE 2A

Without Catalysis

Sodium (13.8 g., 0.6 equivalents) was dissolved in methanol (150 ml). $CF_2ClCFCl_2$ (37.4 g., 0.2 mole) was then added and the reaction mixture refluxed for 20 hours. Distillation of the reaction mixture gave recovered $CF_2ClCFCl_2$ and $CH_3OCF_2CHFCl$ (Product 1). The conversion to $CH_3OCF_2CHFCl$ (Product 1) was 39% and the yield 54%.

EXAMPLE 2B

With Catalysis

In a variation of this process, using a metal salt catalyst, sodium (4.6 g.) was dissolved in methanol (75 ml) and about 0.5 g. $CuCl_2$ added. 18.7 grams (0.1 mole) of $CF_2ClCFCl_2$ was then added. There was no apparent immediate reaction. On addition of a small quantity (less than 0.5 g.) of triethanolamine, the reaction became exothermic with formation of a precipitate. After the reaction subsided, water was added, and 12 g. of product recovered as a precipitate. This product contained 17% unreacted $CF_2ClCFCl_2$, 4.5% $CF_2ClCFHCl$, and 78% $CH_3OCF_2CHFCl$ (Product 1) (about 0.06 moles) as shown by gas chromatography. The conversion to $CH_3OCF_2CHFCl$ (Product 1) was 63% and the yield 71%.

EXAMPLE 3

Different Initial Halogenated Ethane

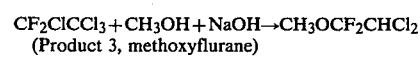
$CF_2ClCCl_3 + CH_3OH + NaOH \rightarrow CH_3OCF_2CHCl_2$
(Product 3, methoxyflurane)

EXAMPLE 3A

Without Catalysis

A mixture of $CF_2ClCCl_3$ (20 g., 0.1 mole), methanol (100 ml) and 50% aqueous sodium hydroxide solution (20 g, 0.25 mole) was refluxed for five hours. The reaction mixture was poured into water to yield 12.4 g. of water insoluble product containing 45% of $CH_3OCF_2CHCl_2$.

Methoxyflurane is a valuable inhalant anesthetic.

EXAMPLE 3B

With Catalysis

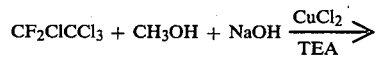
$CF_2ClCCl_3 + CH_3OH + NaOH \xrightarrow[\text{TEA}]{\text{CuCl}_2}$ $CH_3OCF_2CHCl_2$ (Product 3, methoxyflurane)

A mixture of $CF_2ClCCl_3$ (20 g., 0.1 mole), 50% aqueous sodium hydroxide (20 g., 0.25 mole), methanol (100 ml), $CuCl_2$ (0.5 g.) and TEA (triethanolamine) (0.5 g.) was refluxed for five hours. The reaction mixture was poured into water to give 11.2 g. of product containing 96.88% of $CH_3OCF_2CHCl_2$. The conversion to CH$_3$OCF$_2$CHCl$_2$ (Product 3) was about 66% and the yield about 66%.

EXAMPLE 4

Use of Different Metallic Catalysts

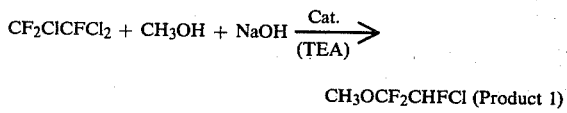

A mixture of CF$_2$ClCFCl$_2$ (94 g., 0.5 mole), methanol (500 ml), 50% aqueous sodium hydroxide (120 g., 1.5 moles) was refluxed for twenty-four hours and the product isolated by distillation and analyzed by gas chromatography to determine the amount of unrecovered unreacted CF$_2$ClCFCl$_2$ and the amount of CF$_3$OCF$_2$CHFCl (Product 1) formed. The effect of metallic catalysts with and without added triethanolamine on the yields and conversions was determined by the following demonstrations of the reaction, which are summarized in tabular form:

| (TEA = Triethanolamine) Catalysts | | CH$_3$OCF$_2$CHFCl (Product 1) | |
|---|---|---|---|
| | | Conversion, % | Yield, % |
| 5 g CrCl$_3$, | 5 g TEA | 63 | 62 |
| 5 g CrCl$_3$, | — | 64 | 73 |
| 5 g VCl$_3$, | 5 g TEA | 77 | 80 |
| 5 g VCl$_3$, | — | 65 | 72 |
| 1.4 g AgCl, | 5 g TEA | 41 | 68 |
| 5 g AgCl, | 5 g TEA | 66 | 75 |
| 9.5 g CoCl$_2$, | 5 g TEA | 31 | 89 |
| 4.8 g RbCl, | 5 g TEA | 47 | 81 |
| 7.9 g MnCl$_2$, | 10 g TEA | 53 | 71 |
| 7.9 g MnCl$_2$, | — | 24 | 65 |
| 10 g MoCl$_5$, | — | 88 | 88 |
| 5 g CuCl$_2$, | 5 g TEA | 80 | 85 |
| 5 g Cu, | — | 50 | 71 |
| 5 g Cu, | 5 g TEA | 56 | 65 |
| 5 g Cu(NO$_3$)$_2$, | 5 g TEA | 70 | 74 |
| 5 g Cu(SO$_4$), | 5 g TEA | 73 | 75 |
| 5 g CuO, | 5 g TEA | 64 | 73 |
| 5 g Cu(OAc)$_2$, | 5 g TEA | 76 | 79 |
| 5 g Al(Cl$_2$)$_3$, | 5 g TEA | 40 | 72 |
| 5 g Al(Cl)$_3$, | — | 36 | 67 |
| 5 g FeCl$_3$, | 5 g TEA | No Conversion | |
| 5 g FeCl$_3$, | — | 40 | 69 |

EXAMPLE 5

Use of Different Amine Catalysts, All with CuCl$_2$

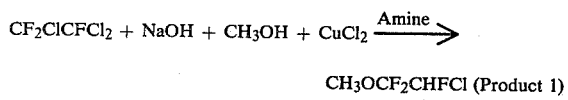

A mixture of CF$_2$ClCFCl$_2$ (94 g., 0.5 mole), 50% aqueous sodium hydroxide solution (120 g, 1.5 mole), methanol (500 ml), CuCl$_2$ (5 g.), and an amine catalyst, was refluxed for 24 hours. The CH$_3$OCF$_2$CHFCl product and recovered unreacted CF$_2$ClCFCl$_2$ were recovered by distillation and analyzed by gas chromatography. Yields and conversions were calculated from the chromatographic analyses.

The yields and conversions when different amines were used are as follows:

| Amine | | Conversion, % | Yield, % |
|---|---|---|---|
| Pyridine | (3 g) | 48 | 70 |
| Ethanolamine | (2.5 g) | 83 | 85 |
| Ethylene diamine | (2.1 g) | 73 | 81 |
| Triethylene tetramine | (2.5 g) | 80 | 80 |
| N,N,N—trimethyl ethylene diamine | (3.6 g) | 81 | 81 |
| N,N—diethylethylene diamine | (4 g) | 81 | 81 |
| 1,2-cyclohexylene-dinitrilo acetic acid | (12 g) | 44 | 63 |
| 3-dimethylamino propyl-amine | (3.6 g) | 55 | 66 |
| Ethylenediamine tetra acetic acid | (10.2 g) | 46 | 74 |
| Diazo bicyclo (2,2,2) octane | (3.9 g) | 51 | 73 |
| N—(2-amino ethyl mor-pholine) | (4.6 g) | 61 | 81 |

A repetition of the reaction but using as catalysts 5 g. VCl$_3$ and 12 g. benzyl trimethyl ammonium methoxide produced a conversion of 35% and a yield of 73%; and repetition with 5 g. VCl$_3$ and 6.3 g. ethanolamine produced a conversion of 71% and a yield of 84%. The combination of 5 g. VCl$_3$ with 3.4 g. N,N,N-trimethylenediamine led to a conversion of 61% and a yield of 82%, whereas the combination of 5 g. of MOCl$_5$ with 5.3 g. ethanolamine produced a conversion of 27% and a yield of 69%, and the combination of 5 g. of MoCl$_5$ with 3.2 g. triethylene tetramine produced a conversion of 81%.

Other combinations of catalysts that have been used in this reaction, with comparable results, include the following:

| Inorganic Catalytic Component | Amine Catalytic Component |
|---|---|
| MoO$_3$, 5 g. | TEA, 12.5 g. |
| MoO$_3$, 5 g. | triethylenetetra-amine, 3.2 g. |

EXAMPLE 6

Catalyzed Dechlorination, Methanol Addition Reaction; With Product Fractionation by Means of an Azeotrope CF$_2$ClCFCl$_2$+CH$_3$OH+NaOH→CH$_3$OCF$_2$CHFCl (Product 1)

A mixture of CF$_2$ClCFCl$_2$ (470 g., 2.5 mole), methanol (1 liter), 50% aqueous sodium hydroxide (600 g., 7.5 moles), CuCl$_2$ (25 g), and triethanolamine (10 g.) was refluxed for seven hours, allowed to stand at room temperature for 16 hours, then refluxed for an additional eight hours.

Water (500 ml) was added and the reaction mixture fractionated to give 68 g. of product, fraction 6a, b.p. 35°–46°, and 286 g. of product, fraction 6b, b.p. 56°.

The lower boiling fraction 6a, was 78% CF$_2$ClCFCl$_2$ and 12% CH$_3$OCF$_2$CHFCl (Product 1) as shown by gas chromatography.

The higher boiling fraction, 6b, was an azeotrope of CH$_3$OCF$_2$CHFCl (Product 1) and methanol, b.p. 56°, which was washed with water to give 224 g. of CH$_3$OCF$_2$CHFCl (Product 1) containing 1.39% of CF$_2$ClCFCl$_2$. The yield of Product 1 was based on theoretical 100% conversion of CF$_2$ClCFCl$_2$ was about 2% in fraction 6a and about 60.5% in fraction 6b, with a total yield of about 62.5%.

The present invention can thus make use of specific catalysts and an economical, readily available reactant, $CF_2ClCFCl_2$, for the efficient synthesis of a valuable ether product. While this ether product has primary present interest as an intermediate, it and other ether products that can be prepared by the process of this invention are useful as fumigants, solvents, chemical intermediates, and in some cases as relatively inert reaction media.

The process has the advantage of being highly specific, in the sense that few unwanted materials appear in the reaction mixture produced. Product recoveries and purifications are thus facilitated and made less expensive. The process also provides new ways to synthesize valuable materials.

While the invention has been disclosed herein by reference to the details of preferred embodiments, it is to be understood that the disclosure is intended in an illustrative sense, and it is contemplated that modifications may be made in the process within the spirit of the invention and the scope of the appended claims.

What is claimed is:

1. A process comprising reacting, in the liquid phase, a compound of the formula:

$$CF_2X\text{-}CY_2Z$$

where
X or Br or Cl;
Y is Br or Cl; and
Z is Br, Cl, or F;
with a primary or secondary alkanol and an inorganic base, in the presence of a catalyst selected from the group consisting of copper, the salts of copper, silver, cobalt, rubidium, aluminum, manganese, nickel, molybdenum, chromium, antimony, and vanadium, the primary, secondary and tertiary alkanol amines and mixtures of any two or more thereof, and recovering an ether reaction product.

2. A process in accordance with claim 1, including the step of distilling the reactants and recovering the reaction products as a distillate.

3. A process in accordance with claim 1 or 2 where the initial reactant is $CF_2ClCFCl_2$.

4. A process in accordance with claim 1 or 2 where the initial reactant is $CF_2ClCCl_3$.

5. A process in accordance with claim 1 or 2 wherein the alkanol is a lower alkanol.

6. A process in accordance with claim 1 or 2 wherein the alkanol is a lower alkanol, and the catalyst comprises a combination of triethanolamine and copper chloride.

7. A process comprising reacting with a perhalogenated ethane, a primary or secondary alkanol and an inorganic base, wherein the perhalogenated ethane is selected from the group consisting of:
$CF_2ClCCl_2F$
$CF_2ClCBr_2F$
$CF_2ClCBrClF$
$CF_2ClCCl_3$
$CF_2ClCCl_2Br$
$CF_2ClCBr_3$
$CF_2ClCBr_2Cl$
$CF_2BrCCl_2F$
$CF_2BrCBr_2F$
$CF_2BrCBrClF$
$CF_2BrCCl_3$
$CF_2BrCCl_2Br$
$CF_2BrCBr_3$
$CF_2BrCBr_2Cl$
and the reaction is conducted in the liquid phase, and in the presence of a catalyst selected from the group consisting of copper, the salts of copper, silver, cobalt, rubidium, aluminum, manganese, nickel, molybdenum, chromium, antimony, and vanadium, the primary, secondary and tertiary alkanol amines and mixtures of any two or more thereof, and recovering an ether reaction product.

8. A process in accordance with claim 7 wherein the alkanol is a lower alkanol.

9. A process in accordance with claim 7 wherein the alkanol is a lower alkanol, and the catalyst comprises a combination of triethanolamine and copper chloride.

10. A processing comprising reacting $$CF_2ClCFCl_2$$

with methanol and an inorganic base in the liquid phase, and in the presence of a catalyst selected from the group consisting of copper, the salts of copper, silver, cobalt, rubidium, aluminum, manganese, nickel, molybdenum, chromium, antimony, and vanadium, the primary, secondary and tertiary alkanol amines and mixtures of any two or more thereof and recovering by distillation from the reaction mixture an azeotrope of methanol and $CH_3OCF_2CHFCl$.

11. A process in accordance with claim 10 wherein the catalyst is a combination of triethanolamine and copper chloride.

* * * * *